United States Patent [19]

Sweet

[11] Patent Number: 4,559,070
[45] Date of Patent: * Dec. 17, 1985

[54] PROCESS FOR DEVOLATILIZING NATURAL GAS LIQUIDS

[75] Inventor: Welby C. Sweet, Jackson, Mich.

[73] Assignee: Marathon Oil Company, Findlay, Ohio

[*] Notice: The portion of the term of this patent subsequent to Apr. 9, 2002 has been disclaimed.

[21] Appl. No.: 692,131

[22] Filed: Jan. 17, 1985

Related U.S. Application Data

[63] Continuation-in-part of Ser. No. 567,716, Jan. 3, 1984, Pat. No. 4,509,967.

[51] Int. Cl.$^4$ ................................................ F25J 3/02
[52] U.S. Cl. ............................................ 62/17; 55/68
[58] Field of Search ................... 208/308, 310 R, 311, 208/318, 321, 322, 340, 341, 343; 62/17, 20, 23, 24, 27-29, 31, 32, 34; 55/68

[56] References Cited

U.S. PATENT DOCUMENTS

| | | | |
|---|---|---|---|
| 3,292,380 | 12/1966 | Bucklin | 62/20 |
| 4,421,535 | 12/1983 | Mehra | 62/17 |
| 4,509,967 | 4/1985 | Sweet | 62/17 |

Primary Examiner—Frank Sever
Attorney, Agent, or Firm—Jack L. Hummel; Rodney F. Brown

[57] ABSTRACT

A natural gas liquid which has been cryogenically extracted from a natural gas feed is devolatized by removing a portion of the ethane from the liquid. The natural gas feed stream is initially split into two streams, the smaller part of the stream being fed to the bottom of a demethanizing absorber at a low temperature and the larger part of the stream being fed to the top of the absorber at a substantially lower cryogenic temperature. A methane-rich gas product is recovered from the top of the absorber while the methane-lean liquid in the bottom of the absorber is fed to a non-cryogenic deethanizer. A portion of the volatiles in the methane-lean liquid are removed in the deethanizer leaving a devolatilized natural gas liquid product.

18 Claims, 2 Drawing Figures

PROCESS FOR DEVOLATILIZING NATURAL GAS LIQUIDS

DESCRIPTION

This is a continuation-in-part of application Ser. No. 567,716, filed on Jan. 3, 1984, now U.S. Pat. No. 4,509,967.

TECHNICAL FIELD

The invention is a process for devolatilizing natural gas condensates and more specifically a process for partially deethanizing natural gas liquids which have been cryogenically extracted from a natural gas feed.

BACKGROUND ART

Hydrocarbon-containing gas, known generally as natural gas, is produced from natural gas wells, oil wells or hydrocarbon refining processes. Natural gas contains a number of combustible hydrocarbon and non-combustible inorganic constituents which have a broad range of molecular weights and boiling points. Natural gas constituents are normally in a gaseous state at atmospheric conditions of temperature and pressure. However, temperature and pressure vary widely from atmospheric conditions when storing or transporting natural gas causing the heavier, higher boiling point hydrocarbons to condense from the gas to a liquid state. Many problems accompany the handling of the resulting two-phase composition. Condensed natural gas liquids, which impede flow by accumulating in pipelines and attendant equipment, are a primary problem.

Handling of natural gas is simplified, if the lighter gases are separated from the readily condensable, heavier hydrocarbons so that the heavier hydrocarbons may be stored or transported separately in a liquid state, i.e. as natural gas liquids. Separation of the natural gas liquids from the lighter gases also enhances the marketability of specific natural gas products.

A number of processes have been described in the art for separating the lighter gaseous constituents from the heavier, higher boiling point hydrocarbons in a natural gas feed. A conventional means for separating the natural gas constituents is to pass the gas through an absorption tower wherein the higher boiling point hydrocarbons are stripped from the gas stream upon contact with a liquid absorbant. Such methods are often more effective when operated cryogenically. U.S. Pat. Nos. 4,318,723 to Holmes et al, 4,157,904 to Campbell et al, 3,359,743 to DiNapoli and 3,846,993 to Bates all describe cryogenic separation processes whereby the temperature of a natural gas is reduced either by rapid expansion or heat exchange. The resulting condensed liquids are separated from the gas in a cryogenic column.

U.S. Pat. Nos. 4,285,708 to Politte et al and 4,128,410 to Bacon and Gulby, J. G., "Options for Ethane Rejection in the Cryogenic Expander Plant," preprint 58th Annual GPA Conv. March 1979, teach cryogenic processes, which reduce the amount of ethane in condensed natural gas liquid to minimize the vapor pressure of the liquid. Bacon and Politte et al are staged processes. Bacon cools the gas by heat exchange with a refrigerant to condense the higher boiling point hydrocarbons. The cooled stream is fed to a separator where the uncondensed gas is removed as pipeline gas. The condensed hydrocarbons are fed to a fractionating tower to remove ethane from the condensate before recovering the condensate as liquid product. Politte et al deethanizes a natural gas feed by splitting it and feeding one stream directly to a deethanizer while feeding the other stream to a stabilizer to remove the heavier components as liquids. The overhead vapor from the stabilizer is fed to the deethanizer to complete the separation of liquids and gases therein.

Non-cryogenic processes for separating readily condensable, heavier, higher boiling point hydrocarbons from a natural gas feed generally do not produce a sufficiently devolatilized natural gas liquid. The vapor pressure of the natural gas liquid is too high to safely store or transport the liquid by conventional means. The above-cited cryogenic processes more effectively separate the gases and liquids in a natural gas feed to produce a less volatile liquid. However, the substantial additional cost of cryogenically designed equipment and energy required to operate the equipment offset the advantage of these cryogenic processes.

A process is needed to separate the heavier natural gas liquids from the lighter gases in a natural gas feed. More specifically, a process is needed, which sufficiently reduces the vapor pressure of the natural gas liquid by removing a portion of the ethane therefrom to allow safe handling of the liquid.

DISCLOSURE OF THE INVENTION

The present invention is a process for separating a natural gas feed into heavier, higher boiling point hydrocarbons and lighter gases by condensing the natural gas liquid, separating the gas and liquid phases, and removing a portion of the ethane and substantially all of the methane from the liquid product. The natural gas feed may be obtained from any natural gas source including oil and gas production wells or petroleum refining processes. The natural gas feed contains: (1) combustible, lighter, hydrocarbon gases, such as methane, (2) heavier hydrocarbon constituents, such as ethane, propane, butane, pentane, etc., and (3) non-combustible inorganic gases such as nitrogen, carbon dioxide, helium, etc. The natural gas liquid produced according to the instant process is sufficiently devolatilized to enable safe transportation and storage of it by conventional means.

Basically the process employs two distinct separation unit operations with intervening heat transfer and expansion apparatus. The lighter gases are separated from the heavier hydrocarbons in the first unit, a cryogenic demethanizing absorber. The gas product is taken off the top of the absorber and discharged to a pipeline. The liquids are withdrawn from the bottom of the absorber and fed to the second unit, a non-cryogenic product deethanizer wherein a portion of the ethane is separated from the liquid product. The partially deethanized natural gas liquid is withdrawn from the bottom of the deethanizer in a devolatilized condition for transporting. The overhead gases from the deethanizer are recycled to the demethanizing absorber.

The sizing of the cryogenic demethanizing absorber is minimized by physically splitting the natural gas feed stream at high pressure and near ambient atmospheric temperature into a first and a second stream of like composition before treating the feed. The first stream is fed into the upper portion of the absorber as a two-phase mixture after its temperature and pressure are substantially reduced by heat exchange and expansion. The gas phase is comprised primarily of the lighter constituents (i.e. methane and non-combustible constituents) and some residual heavier hydrocarbons. The liquid phase is comprised of any remaining condensed lighter constituents and substantially all of the heavier hydrocarbons found in the first stream. The second stream, which may contain recycled deethanizer off-gas, is fed into the lower portion of the demethanizing absorber as a two-phase mixture at a temperature substantially above the temperature of the first stream. As a result, the gas phase contains more heavier hydrocarbon and the liquid phase contains fewer lighter constituents than those of the first stream.

Essentially four distinct streams are fed to the absorber, a gas and liquid stream to the upper portion and a gas and liquid stream to the lower portion. However, the effective feeds to the absorber are the gas phase of the lower stream and the liquid phase of the upper stream. The liquid in the lower stream and the gas in the upper stream have little effect in the absorber because they are withdrawn in close proximity to their feed points. Because the two effective feed streams have different compositions due to their phase and temperature differences noted above, they exchange components on contact. The falling liquid absorbs heavier hydrocarbons in the upflowing gas and the upflowing gas strips lighter constituents from the falling liquid as the two streams flow countercurrent in the absorber.

A gas product is recovered at the top of the absorber, which contains relatively few heavier hydrocarbons. The gas is primarily methane and a smaller amount of ethane. The amount of ethane in the gas is regulated by controlling the operating temperature and pressure of the process.

The liquids are withdrawn from the bottom of the absorber and are used to cool the second stream before it is fed to the absorber. Thereafter, the liquids are fed to the deethanizer which can be a staged distillation or packed column. The liquids accumulated in the bottom of the deethanizer are heated, vaporizing the more volatile portion of the liquid. The less volatile unvaporized liquid is recovered as liquid product. Additional liquid product can be recovered, if desired, by refluxing the volatile vapors in an optional condenser after the deethanizer. In any case, all the remaining uncondensed volatile vapors in the process are either recovered as gas product or recycled to the second stream as absorber feed.

The advantages of this process are readily apparent. The process utilizes a deethanizer operated at a non-cryogenic temperature in conjunction with a cryogenic demethanizing absorber. By splitting the feed stream, the cryogenic demethanizing absorber can be sized smaller than one which cryogenically treats the entire unsplit feed stream at once. The operating conditions of the system, including temperature and pressure, can be varied to treat feed types ranging from lean gas, having a relatively low concentration of natural gas liquids, to rich gas, having a relatively high concentration of liquids. These conditions can also be varied to produce somewhat different residual levels of heavier hydrocarbons in the gas product and volatiles in the liquid product. In any case, the final process products are a pipeline gas containing relatively few readily condensable, higher boiling point hydrocarbons and a natural gas liquid having only a small amount of volatile hydrocarbons such that the vapor pressure of the liquid is sufficiently low to enable safe handling thereof.

BEST MODE FOR CARRYING OUT THE INVENTION

The present invention is a process for separating readily condensable, heavier hydrocarbons from lighter gases in a natural gas feed and partially deethanizing the condensed heavier hydrocarbons to reduce their vapor pressure. The initial inlet feed stream to the process is a hydrocarbon-containing gas, generally defined as a natural gas. The natural gas contains non-combustible constituents as well as combustible hydrocarbons. The exact composition of the gas varies depending on its source. Natural gas sources include natural gas or oil production wells and hydrocarbon refining processes. Generally the natural gas is comprised of at least 50 percent methane with the remainder being heavier (i.e. higher molecular weight) hydrocarbons such as ethane, propane, butane, pentane, etc. and non-combustible inorganic constituents such as nitrogen and carbon dioxide. The heavier hydrocarbons are readily condensable at high pressure or low temperature. The condensed heavier hydrocarbons are natural gas liquids.

Figure 1:
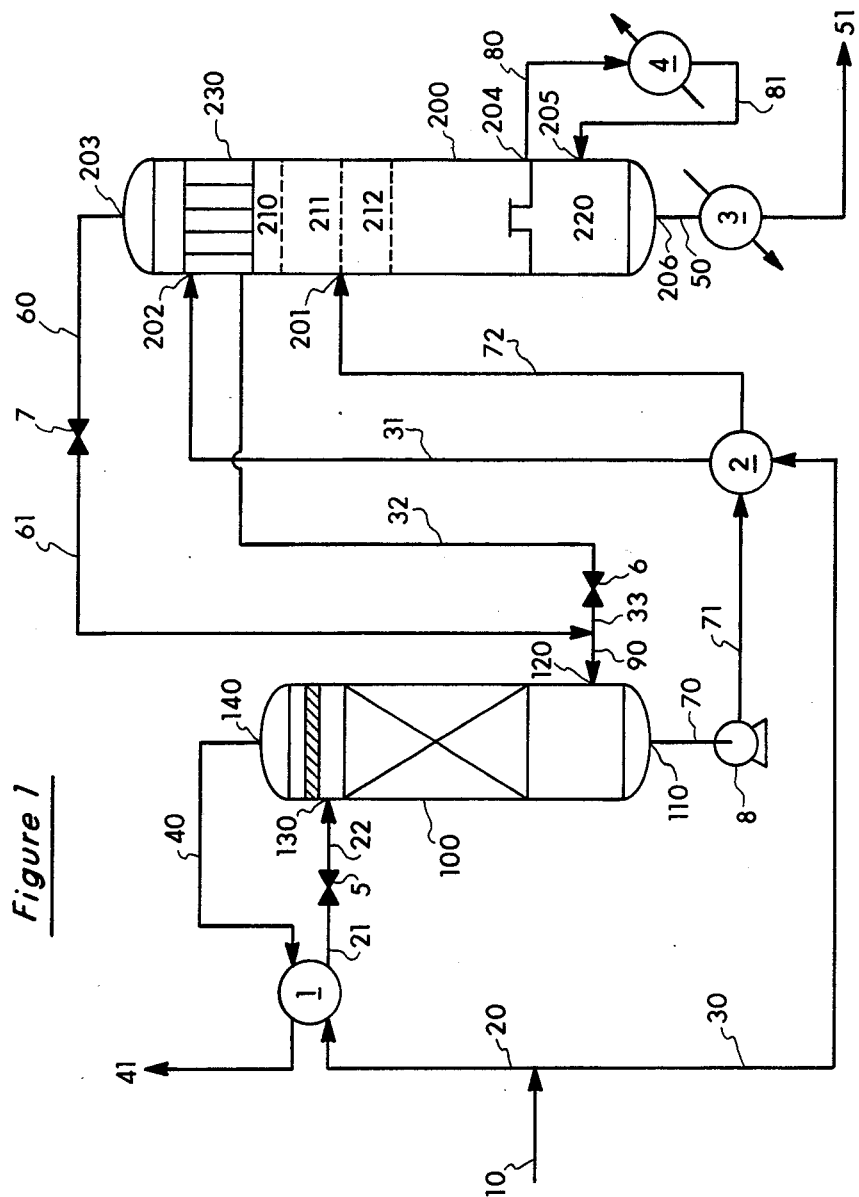
FIG. 1 is a schematic flowsheet of one embodiment of the process described herein containing the demethanizing absorber and product deethanizer, which is a distillation tower with overhead condenser.

Referring to FIG. 1, natural gas feed (10) enters the process at a pressure of about 5516 to 8274 kiloPascals (kPa) and a temperature of about 16° to 49° C. Inlet feed (10) is split into first stream (20) and second stream (30) by any appropriate physical means such that first stream (20) is about 50 to 80 percent of inlet feed (10). The exact fraction of the feed split depends on the composition, pressure and temperature of inlet feed (10). The fraction of the feed split may be readily determined for given values of these parameters to obtain a desired degree of ethane recovery.

First stream (20) is cooled in heat exchange means (1) by absorber outlet gas (40) from demethanizing absorber (100). Additional or alternative cooling of first stream (20) may be provided by an auxiliary refrigerant at this point as well, although not shown herein. Cooled stream (21) is then expanded across expansion means (5) to further reduce its temperature to a cryogenic level and correspondingly reduce its pressure. Cryogenic temperatures, as defined herein, are those below about −28.9° C. At cryogenic temperatures, first stream (22) is a two-phase composition, having a gas and a liquid phase.

Second stream (30) is cooled in heat exchange means (2) by condensed liquids (71) from demethanizing absorber (100). As with first stream (20), second stream (30) can likewise be cooled by an auxiliary refrigerant. Stream (31) is then used as a coolant in overhead condenser (230) wherein vapors (60) from product deethanizer (200) are condensed. Overhead condenser (230) may be physically joined to deethanizer (200) or may be a separately linked unit. In either case, it has the the same function.

Second stream (32) is expanded across expansion means (6) to cool it and reduce its pressure. Second stream (33) is combined with condenser off-gas (61) to be recycled to the absorber. Resulting combined stream (90) is a two-phase composition, having a pressure substantially equal to that of first stream (22), but a temperature substantially higher than first stream (22). The recycle and second stream (90) are fed into the lower portion of the absorber at (120) while the first stream is fed into the upper portion at (130). The gas in the lower feed flows upward through the absorber, stripping the lighter constituents from the liquid. The liquid in the upper feed flows downward countercurrent to the gas, absorbing the heavier, higher boiling point hydrocarbons in the gas. The gas reaching the top of the absorber is removed overhead at (140) as product at a low temperature. It is passed through heat exchange means (1) to cool first stream (20) as noted above. Product gas (41) is methane-rich, containing substantially all of the methane and inorganic gases from the inlet natural gas feed. The amount of ethane retained in the gas product is dependent on the operating conditions of the process.

The methane-lean liquid in the bottom of absorber (70) is withdrawn at (110) at a temperature higher than absorber outlet gas (40). Stream (71) is pumped by pumping means (8) at high pressure into heat exchange means (2) where it cools second stream (30) as noted above. Liquid stream (72) is then fed to the middle of deethanizer (201), i.e. at stage (211) below uppermost stage (210) of the deethanizer. Liquid (72) combines with condenser reflux and flows downward through the deethanizer. Liquids (80) are withdrawn from the deethanizer at level (204) below lowermost stage (212) and fed to reboiler (4) where they are heated. Heated liquid (81) is reinserted into the lower portion of the deethanizer at (205). The more volatile portion of liquid (81) is vaporized in the lower portion of deethanizer (220) and the resulting deethanizer vapor flows through deethanizer (200) countercurrent to the refluxed liquids. The deethanizer vapor passes through deethanizer distillation stages, (210), (211) and (212) and into the overhead condenser (230). The more volatile vapor components, which include methane and a portion of the ethane, remain in the vapor phase while the less volatile, heavier hydrocarbon vapor components are refluxed back into the deethanizer.

The uncondensed vapor (60) is removed from the condenser at (203). At this point, vapor (60) can be recovered as a gas product or recycled to the absorber as shown herein. Vapor (60) is recycled by expanding across expansion means (7) to reduce its pressure and temperature before recycling vapor stream (61) to the bottom of the absorber at (120) in combination with second stream (33).

Liquid product (50) is withdrawn from the bottom of the deethanizer at (206) and cooled in heat exchange means (3). The natural gas liquid product (51) contains a portion of the ethane and substantially all of the heavier, higher boiling point hydrocarbons from the inlet natural gas feed, i.e. propane, butane, pentane, etc., and substantially none of the lighter constituents, i.e. methane, nitrogen, and carbon dioxide. The ethane not in gas product (41) is found in liquid product (51). As noted above, the amount of ethane in this stream is dependent on the composition of the feed gas and the operating conditions of the system. The temperature and pressure may be varied to achieve the desired degree of deethanization of the liquid product. In this manner, the process may be adapted to produce liquids having a range of vapor pressures.

Figure 2:
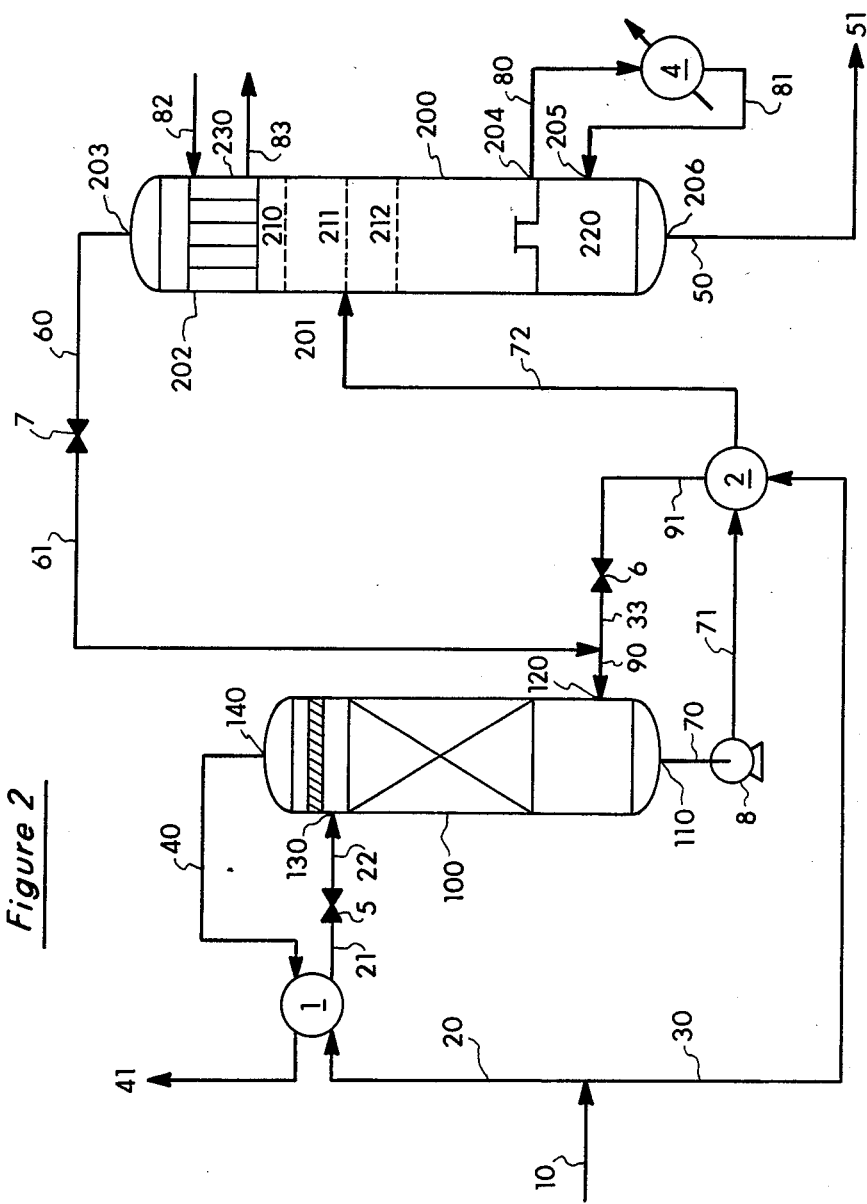
FIG. 2 is a schematic flowsheet of the process modified to maximize ethane recovery in the liquid product.

The above-described process, as shown in FIG. 1, minimizes ethane recovery in the liquid product. Although ethane recovery can be somewhat increased merely by changing the operating conditions of the process, e.g., the use of auxiliary refrigerants in the feed streams as noted above, ethane recovery can be maximized by the modification of the process flowsheet shown in FIG. 2. Referring to FIG. 2, auxiliary refrigerant (82), such as propane, is provided as a coolant in overhead condenser (230), exiting via stream (83). Second stream (30) bypasses overhead condenser (230) and is fed into the bottom of absorber (100) at (120) after second stream (30) is first cooled in heat exchange means (2) and combined with recycle (61) to form stream (90).

FIGS. 1 and 2 both show embodiments of the invention wherein the deethanizer (200) is a staged distillation column with an overhead condenser (230). However, other embodiments are also within the scope of this invention. For example, the deethanizer can be a staged packed column rather than a distillation column. The packed column would perform the same function as the distillation column. Condenser (230) is an optimal step, which may be eliminated in any of these embodiments, in which case stream (72) could be fed to the uppermost stage (210) of the deethanizer rather than at stage (211).

The following examples are particular applications of the process. The examples illustrate how different levels of ethane recovery can be achieved in the liquid product and gas product streams by varying the process conditions. Example 1 maximizes ethane recovery in the liquid product, using the process of FIG. 2, while Example 2 minimizes ethane recovery in the liquid product using the process of FIG. 1. Example 3 achieves an intermediate level of ethane recovery in the liquid product using the process of FIG. 1. The examples are not to be construed as limiting the scope of the present invention.

EXAMPLE 1

A raw natural gas from a wellhead is fed into the system of FIG. 2 at a pressure of 7205 kPa and temperature of 48.9° C. The inlet feed is split into a first and second stream. The first stream, 72% of the inlet feedstream, is fed to a heat exchanger where it is cooled by the absorber outlet gas to a temperature of −58.9° C. It is flashed across an expansion valve to a temperature of −109° C. and a pressure of 1413 kPa. It is then fed into the demethanizing absorber.

The second stream, 28% of the inlet feedstream, is fed to a heat exchanger where it is cooled by the liquid from the absorber bottom to a temperature of −40° C. The second stream is then flashed across an expansion valve and merged with the recycle from the product deethanizer. The combined stream is fed into the bottom of the demethanizing absorber at a temperature of −72.8° C. and a pressure of 1427 kPa. The gas product withdrawn overhead from the demethanizing absorber has a temperature of −108° C. and a pressure of 1412 kPa. The gas product is used to cool the first stream, raising the gas product temperature to 43.3° C. This gas is suitable for pipeline transport.

The phase and composition of the demethanizing absorber inlet and outlet streams are given below in Table 1.

TABLE 1

| | \multicolumn{2}{c}{Top Feed} | \multicolumn{2}{c}{Bottom Feed} | Gas | Raw |
| Component | Liquid | Gas | Liquid | Gas | Product | Liquid |
|---|---|---|---|---|---|---|
| Nitrogen | 0.24 | 2.67 | 0.08 | 1.95 | 2.29 | 0.09 |

TABLE 1-continued

Demethanizing Absorber Streams (Compositions in Mole %)

| Component | Top Feed Liquid | Top Feed Gas | Bottom Feed Liquid | Bottom Feed Gas | Gas Product | Raw Liquid |
|---|---|---|---|---|---|---|
| Carbon Dioxide | 0.09 | 0.01 | 0.10 | 0.07 | 0.03 | 0.18 |
| Methane | 69.96 | 96.69 | 23.32 | 89.31 | 96.91 | 26.79 |
| Ethane | 15.85 | 0.61 | 40.47 | 8.31 | 0.75 | 47.34 |
| Propane | 5.46 | 0.01 | 12.44 | 0.30 | 0.02 | 10.17 |
| i-Butane | 1.82 | 0.0 | 4.89 | 0.03 | 0.0 | 3.34 |
| n-Butane | 3.13 | 0.0 | 8.70 | 0.03 | 0.0 | 5.74 |
| i-Pentane | 0.79 | 0.0 | 2.28 | 0.0 | 0.0 | 1.46 |
| n-Pentane | 1.50 | 0.0 | 4.31 | 0.0 | 0.0 | 2.75 |
| n-Heptane | 1.17 | 0.0 | 3.39 | 0.0 | 0.0 | 2.14 |
| % of Feed | 21.40 | 78.60 | 6.19 | 93.81 | | |

The raw liquid is withdrawn from the absorber bottom at a temperature of −78.3° C. and is used to cool the second stream in a heat exchanger. The heat exchanger raises the temperature of the raw liquid to 15° C. at a pressure of 2758 kPa. The liquid is fed into tray 9 of the deethanizer, which contains 13 trays. The liquid passes down to tray 1 where it is withdrawn, fed to a reboiler and heated to 32.2° C. at a pressure of 2758 kPa. The resulting heated liquid and vapors are fed to the bottom of the deethanizer. The vapors pass up through the deethanizer into the overhead condenser some of which produce a condensate, refluxing back down through the deethanizer. The remaining uncondensed vapors are withdrawn from the condenser at a temperature of −28.9° C. and at a pressure of 2723 kPa. This gas is flashed across an expansion valve to a pressure of 1427 kPa and combined with the second stream to be recycled into the absorber. The heated liquid not vaporized in the reboiler and reflux are withdrawn from the bottom of the deethanizer. The liquid product has a vapor pressure of 2910 kPa at 37.8° C. representing a maximum ethane recovery for the process and the given feed composition. The liquid product is in a condition for storing, transporting or further separation if desired.

The compositions of the initial natural gas inlet feed to the process, final gas product from the absorber, and final liquid product from the deethanizer expressed in mole % are given below in Table 2.

TABLE 2

| Component | Gas Feed | Gas Product | Liquid Product |
|---|---|---|---|
| Nitrogen | 2.15 | 2.29 | 0.0 |
| Carbon Dioxide | 0.03 | 0.03 | 0.08 |
| Methane | 90.97 | 96.91 | 2.39 |
| Ethane | 3.87 | 0.75 | 50.37 |
| Propane | 1.18 | 0.02 | 18.53 |
| i-Butane | 0.39 | 0.0 | 6.20 |
| n-Butane | 0.67 | 0.0 | 10.65 |
| i-Pentane | 0.17 | 0.0 | 2.71 |
| n-Pentane | 0.32 | 0.0 | 5.09 |
| n-Heptane | 0.25 | 0.0 | 3.98 |

EXAMPLE 2

A raw natural gas from a wellhead is fed into the system of FIG. 1 at a pressure of 7205 kPa and a temperature of 48.9° C. The inlet feed is split into a first and second stream. The first stream, 75% of the inlet feedstream, is fed to a heat exchanger where it is cooled by the absorber outlet gas to a temperature of −54.4° C. It is flashed across an expansion valve to a temperature of −104° C. at a pressure of 1413 kPa. It is then fed into the demethanizer absorber.

The second stream, 25% of the inlet feedstream, is fed to a heat exchanger where it is cooled by the liquid from the absorber bottom to a temperature of 10.6° C. The second stream is then fed to the overhead condenser of the deethanizer and heated to a temperature of 23.3° C. It is flashed across an expansion valve and merged with the recycle from the product deethanizer. The combined stream is fed into the bottom of the demethanizing absorber at a temperature of −4.44° C. and a pressure of 1427 kPa. The gas product withdrawn overhead from the demethanizing absorber has a temperature of −92.8° C. and a pressure of 1413 kPa. The gas product is used to cool the first stream, raising the gas product temperature to 43.3° C. This gas is suitable for pipeline transport.

The phase and composition of the demethanizing absorber inlet and outlet streams are given below in Table 3.

TABLE 3

Demethanizing Absorber Streams (Compositions in Mole %)

| Component | Top Feed Liquid | Top Feed Gas | Bottom Feed Liquid | Bottom Feed Gas | Gas Product | Raw Liquid |
|---|---|---|---|---|---|---|
| Nitrogen | 0.17 | 2.47 | 0.04 | 2.03 | 2.22 | 0.06 |
| Carbon Dioxide | 0.10 | 0.02 | 0.01 | 0.03 | 0.03 | 0.02 |
| Methane | 56.94 | 96.42 | 8.51 | 87.67 | 93.75 | 12.01 |
| Ethane | 21.86 | 1.06 | 4.60 | 6.60 | 3.92 | 18.57 |
| Propane | 8.33 | 0.03 | 6.32 | 2.17 | 0.08 | 30.08 |
| i-Butane | 2.75 | 0.0 | 3.12 | 0.39 | 0.0 | 8.59 |
| n-Butane | 4.70 | 0.0 | 7.61 | 0.63 | 0.0 | 14.61 |
| i-Pentane | 1.19 | 0.0 | 4.88 | 0.15 | 0.0 | 3.69 |
| n-Pentane | 2.23 | 0.0 | 12.62 | 0.26 | 0.0 | 6.94 |
| n-Heptane | 1.74 | 0.0 | 52.28 | 0.08 | 0.0 | 5.42 |
| % of Feed | 14.32 | 85.68 | 0.30 | 99.70 | | |

The raw liquid is withdrawn from the absorber bottom at a temperature of −37.2° C. and is used to cool the second stream in a heat exchanger. The heat exchanger raises the temperature of the raw liquid to 43.3° C. at a pressure of 2758 kPa. The liquid is fed into tray 9 of the deethanizer, which contains 13 trays. The liquid passes down to tray 1 where it is withdrawn, fed to a reboiler and heated to 113° C. at a pressure of 2758 kPa. The resulting heated liquid and vapors are fed to the bottom of the deethanizer. The vapors pass up through the deethanizer into the overhead condenser some of which produce a condensate, refluxing back down through the deethanizer. The remaining uncondensed vapors are withdrawn from the condenser at a temperature of 13.3° C. and at a pressure of 2723 kPa. This gas is flashed across an expansion valve to a pressure of 1427 kPa and combined with the second stream to be recycled into the absorber. The heated liquid not vaporized in the reboiler and reflux are withdrawn from the bottom of the deethanizer and cooled to 48.9° C. The liquid product has a vapor pressure of 614 kPa at 37.8° C. representing a minimum ethane recovery for the process and the given feed composition. The liquid product is in a condition for storing, transporting or further separation if desired.

The compositions of the initial natural gas inlet feed to the process, final gas products from the absorber, and final liquid product from the deethanizer expressed in mole % are given below in Table 4.

TABLE 4

| Component | Gas Feed | Gas Product | Liquid Product |
|---|---|---|---|
| Nitrogen | 2.15 | 2.22 | 0.0 |
| Carbon Dioxide | 0.03 | 0.03 | 0.0 |
| Methane | 90.97 | 93.75 | 0.0 |

TABLE 4-continued

| Component | Gas Feed | Gas Product | Liquid Product |
|---|---|---|---|
| Ethane | 3.87 | 3.92 | 2.24 |
| Propane | 1.18 | 0.08 | 37.15 |
| i-Butane | 0.39 | 0.0 | 13.09 |
| n-Butane | 0.67 | 0.0 | 22.57 |
| i-Pentane | 0.17 | 0.0 | 5.73 |
| n-Pentane | 0.32 | 0.0 | 10.79 |
| n-Heptane | 0.25 | 0.0 | 8.43 |

EXAMPLE 3

A raw natural gas from a wellhead is fed into the system of FIG. 1 at a pressure of 7205 kPa and a temperature of 48.9° C. The inlet feed is split into a first and second stream. The first stream, 75% of the inlet feed stream, is fed to a heat exchanger where it is cooled by the absorber outlet gas to a temperature of −55.6° C. It is flashed across an expansion valve to a temperature of −105° C. and a pressure of 1413 kPa. It is then fed into the demethanizing absorber.

The second stream, 25% of the inlet feed stream, is fed to a heat exchanger where it is cooled by the liquid from the absorber bottom to a temperature of −18.9° C. The second stream is then fed to the overhead condenser of the deethanizer and raised to a temperature of −2.78° C. It is flashed across an expansion valve and merged with the recycle from the product deethanizer. The combined stream is fed into the bottom of the demethanizing absorber at a temperature of −35° C. and a pressure of 1427 kPa. The gas product withdrawn overhead from the demethanizing absorber has a temperature of −97.2° C. and a pressure of 1413 kPa. The gas product is used to cool the first stream, raising the gas product temperature to 43.3° C. This gas is suitable for pipeline transport.

The phase and composition of the demethanizing absorber inlet and outlet streams are given below in Table 5.

TABLE 5

Demethanizing Absorber Streams (Compositions in Mole %)

| Component | Top Feed Liquid | Top Feed Gas | Bottom Feed Liquid | Bottom Feed Gas | Gas Product | Raw Liquid |
|---|---|---|---|---|---|---|
| Nitrogen | 0.18 | 2.49 | 0.05 | 2.00 | 2.25 | 0.07 |
| Carbon Dioxide | 0.10 | 0.02 | 0.02 | 0.03 | 0.03 | 0.03 |
| Methane | 58.87 | 96.50 | 11.88 | 87.65 | 94.94 | 16.52 |
| Ethane | 20.83 | 0.97 | 11.59 | 8.22 | 2.72 | 38.31 |
| Propane | 7.88 | 0.03 | 9.95 | 1.29 | 0.06 | 18.15 |
| i-Butane | 2.64 | 0.0 | 7.04 | 0.27 | 0.0 | 5.82 |
| n-Butane | 4.52 | 0.0 | 16.96 | 0.40 | 0.0 | 10.02 |
| i-Pentane | 1.15 | 0.0 | 7.84 | 0.06 | 0.0 | 2.54 |
| n-Pentane | 2.15 | 0.0 | 16.93 | 0.08 | 0.0 | 4.79 |
| n-Heptane | 1.68 | 0.0 | 17.73 | 0.0 | 0.0 | 3.74 |
| % of Feed | 14.85 | 85.15 | 1.27 | 98.73 | | |

The raw liquid is withdrawn from the absorber bottom at a temperature of −56.7° C. and is used to cool the second stream in a heat exchanger. The heat exchanger raises the temperature of the raw liquid to 43.3° C. at a pressure of 2758 kPa. The liquid is fed into tray 9 of the deethanizer, which contains 13 trays. The liquid passes down to tray 1 where it is withdrawn, fed to a reboiler and heated to 60.0° C. at a pressure of 2758 kPa. The resulting heated liquid and vapors are fed to the bottom of the deethanizer. The vapors pass up through the deethanizer into the overhead condenser some of which produce a condensate, refluxing back down through the deethanizer. The remaining uncondensed vapors are withdrawn from the condenser at a temperature of −13.3° C. and a pressure of 2723 kPa. This gas is flashed across an expansion valve to a pressure of 1427 kPa and combined with the second stream to be recycled into the absorber. The heated liquid not vaporized in the reboiler and reflux are withdrawn from the bottom of the deethanizer and cooled to 48.9° C. The liquid product has a vapor pressure of 1882 kPa at 37.8° C. The liquid product is in a condition for storing, transporting or further separation if desired.

The compositions of the initial natural gas inlet feed to the process, final gas product from the absorber, and final liquid product from the deethanizer expressed in mole % are given below in Table 6.

TABLE 6

| Component | Gas Feed | Gas Product | Liquid Product |
|---|---|---|---|
| Nitrogen | 2.15 | 2.25 | 0.0 |
| Carbon Dioxide | 0.03 | 0.03 | 0.01 |
| Methane | 90.97 | 94.94 | 1.46 |
| Ethane | 3.87 | 2.72 | 29.72 |
| Propane | 1.18 | 0.06 | 26.50 |
| i-Butane | 0.39 | 0.0 | 9.14 |
| n-Butane | 0.67 | 0.0 | 15.75 |
| i-Pentane | 0.17 | 0.0 | 4.00 |
| n-Pentane | 0.32 | 0.0 | 7.53 |
| n-Heptane | 0.25 | 0.0 | 5.89 |

The three examples provided above all treat a natural gas feed stream having a common, relatively lean composition. It is apparent that the present process may be used to treat richer or leaner natural gas feeds by changing such process operating conditions as temperature, pressure and fractional feed division. Where the amount of liquids in the natural gas feed exceeds the capacity of the system as in a rich natural gas, the initial natural gas feed can be treated by additional refrigeration at the front end of the process before the feed is split to remove some of the liquids.

While the foregoing embodiment of the invention has been described and shown, it is understood that all alternatives and modifications, such as those suggested, and others may be made thereto, and fall within the scope of the invention.

I claim:

1. A process to devolatilize a natural gas liquid obtained from a natural gas feed comprised of methane, ethane and other heavier hydrocarbons, the process comprising the steps of:
    (a) dividing said natural gas feed into a first stream and a second stream, the two streams having the same composition;
    (b) reducing the temperature and pressure of said first and second streams such that each said stream has a distinct liquid phase and a distinct gas phase, said first stream has a temperature substantially lower than said second stream, and at least said first stream has a cryogenic temperature;
    (c) feeding said first stream into the upper portion of a demethanizing absorption means and said second stream into the lower portion of said absorption means;
    (d) recovering a methane-rich gas product from the top of said absorption means and a methane-lean natural gas liquid from the bottom of said absorption means;
    (e) feeding said methane-lean natural gas liquid into a deethanizer means wherein an uncondensed vapor comprised of a portion of the ethane and substantially all of the methane in said methane-lean natural gas liquid is separated from said methane-lean natural gas liquid at a non-cryogenic temperature;

(f) recovering said uncondensed vapor from the top of said deethanizer means; and (g) recovering a partially deethanized natural gas liquid product from the bottom of said deethanizer means comprised of the remaining portion of ethane and heavier hydrocarbons in said methane-lean natural gas liquid and which is less volatile than said methane-lean natural gas liquid.

2. The process of claim 1 wherein said methane-lean natural gas liquid cools said second stream in a heat exchange means to initiate the temperature reduction of step (b) prior to feeding said natural gas liquid to said deethanizer means.

3. The process of claim 1 wherein the temperature and pressure of said first and second streams are reduced a predetermined amount to achieve a predetermined level of ethane recovery in said methane-rich gas product and natural gas liquid product.

4. The process of claim 1 wherein the relative fraction of said natural gas feed divided into said first and second streams is predetermined to achieve a predetermined level of ethane recovery in said methane-rich gas product and natural gas liquid product.

5. The process of claim 4 wherein about 50 to about 80% of said natural gas feed is divided into said first stream and about 50 to about 20% of said natural gas feed is divided into said second stream.

6. The process of claim 1 wherein the pressure of said natural gas feed is about 5516 to about 8274 kPa and the temperature of said natural gas feed is about 16° to about 49° C.

7. The process of claim 1 wherein said deethanizer means is comprised of a column, having a plurality of vertically spaced distillation stages, and a condenser.

8. The process of claim 7 wherein said methane-lean natural gas liquid is fed to said deethanizer means at an intermediate point in said column between the uppermost and lowermost stages.

9. The process of claim 8 wherein said methane-lean natural gas liquid, having passed below said lowermost stage, is sufficiently heated to vaporize the more volatile portion of said natural gas liquid into a deethanizer vapor and the remaining less volatile unvaporized portion of said natural gas liquid recovered as said partially deethanized natural gas liquid product.

10. The process of claim 9 wherein said deethanizer vapor is passed through said column into said condenser where the less volatile portion of said deethanizer vapor is refluxed and recovered as partially deethanized natural gas liquid product and the more volatile portion of said deethanizer vapor not refluxed is recycled to said absorption means as said uncondensed vapor.

11. The process of claim 9 wherein said natural gas liquid is heated in a reboiler.

12. The process of claim 7 wherein said cooled second stream is circulated through said condenser as a coolant prior to recycling said uncondensed vapor into said second stream.

13. The process of claim 7 wherein ethane recovery in said natural gas liquid product is maximized by circulating an auxiliary refrigerant through said condenser as a coolant.

14. The process of claim 1 wherein said methane-rich gas product cools said first stream in a heat exchange means to initiate the temperature reduction of step (b).

15. The process of claim 1 wherein said first stream is expanded across a first expansion means to effect the temperature and pressure reduction of step (b).

16. The process of claim 1 wherein said second stream is expanded across an expansion means to effect the temperature and pressure reduction of step (b).

17. The process of claim 1 further comprising recycling said uncondensed vapor into said second stream of step (c) prior to feeding said second stream into said absorption means.

18. The process of claim 1 wherein said uncondensed vapor is a second methane-rich gas product.

* * * * *